(12) United States Patent
Hamano (10) Patent No.: US 7,675,425 B2
(45) Date of Patent: Mar. 9, 2010

(54) LIQUID DISCHARGE DEVICE CAPABLE OF SELF-DIAGNOSIS OF DISCHARGE FUNCTIONS

(75) Inventor: Soji Hamano, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 544 days.

(21) Appl. No.: 11/730,947

(22) Filed: Apr. 5, 2007

(65) Prior Publication Data

US 2007/0235026 A1    Oct. 11, 2007

(30) Foreign Application Priority Data

Apr. 10, 2006    (JP)    ............................. 2006-107082

(51) Int. Cl.
*G08B 21/00*    (2006.01)
(52) U.S. Cl. ........................ 340/635; 222/75; 379/29.11
(58) Field of Classification Search ................. 340/635; 222/75; 379/29.11
See application file for complete search history.

(56) References Cited

U.S. PATENT DOCUMENTS

| | | | | | |
|---|---|---|---|---|---|
| 3,050,673 | A | * | 8/1962 | Widmer ...................... 320/166 |
| 4,387,447 | A | * | 6/1983 | Klaas et al. ............. 365/185.16 |
| 4,992,836 | A | * | 2/1991 | Sicard ......................... 361/111 |
| 5,173,832 | A | * | 12/1992 | Giorgetta et al. .............. 361/88 |
| 5,363,842 | A | * | 11/1994 | Mishelevich et al. ... 128/200.14 |
| 6,366,868 | B2 | * | 4/2002 | Freudenberg et al. ....... 702/115 |
| 6,820,474 | B2 | * | 11/2004 | Rueger et al. ............. 73/114.51 |
| 7,380,449 | B2 | * | 6/2008 | Mrosik et al. ............. 73/114.45 |
| 7,445,305 | B2 | * | 11/2008 | Kondoh ........................ 347/11 |
| 7,456,545 | B2 | * | 11/2008 | Huber et al. ........... 310/316.03 |
| 7,525,783 | B2 | * | 4/2009 | Chemisky et al. ........... 361/139 |
| 2002/0008440 | A1 | * | 1/2002 | Hedenetz et al. ....... 310/316.03 |
| 2002/0069459 | A1 | * | 6/2002 | Pondelick et al. .............. 4/431 |
| 2002/0162539 | A1 | * | 11/2002 | Bolz et al. ................... 123/479 |
| 2003/0221478 | A1 | * | 12/2003 | Hart et al. ................... 73/118.1 |
| 2004/0008032 | A1 | * | 1/2004 | Rueger et al. ................ 324/522 |
| 2004/0261509 | A1 | * | 12/2004 | Mrosik et al. ............. 73/119 A |
| 2006/0067024 | A1 | * | 3/2006 | Chemisky et al. ........... 361/139 |
| 2006/0262150 | A1 | * | 11/2006 | Kondoh .......................... 347/9 |
| 2007/0109362 | A1 | * | 5/2007 | Hori et al. ...................... 347/65 |
| 2007/0182280 | A1 | * | 8/2007 | Huber et al. ........... 310/316.03 |
| 2007/0235026 | A1 | * | 10/2007 | Hamano ................ 128/200.14 |
| 2007/0256688 | A1 | * | 11/2007 | Schuster et al. ........ 128/200.23 |

* cited by examiner

*Primary Examiner*—Daniel Wu
*Assistant Examiner*—Bradley E Thompson
(74) *Attorney, Agent, or Firm*—Fitzpatrick, Cella, Harper & Scinto (57) ABSTRACT

A liquid discharging device includes: a discharge head mounting unit having first and second electrical terminals; a power source; a switch controlling connection between the power source and the electrical terminals; and a control unit controlling the switch; wherein a driving circuit driving a liquid discharge head is closed by attachment thereof to the mounting unit; the power source can selectively output multiple voltages; and the control unit selectively effects a state for supply of a discharge electrical power, in which electric power sufficient for a discharging actuator of the discharge head to discharge liquid is supplied thereto by controlling the switch, and a state for diagnosis, in which, wherein electric power insufficient for the discharging actuator to discharge liquid is supplied thereto by controlling the switch, and in which the voltage of at least one of the terminals is measured, and information of the state of the power source, discharging actuator, and driving circuit, is obtained.

8 Claims, 9 Drawing Sheets

LIQUID DISCHARGE DEVICE CAPABLE OF SELF-DIAGNOSIS OF DISCHARGE FUNCTIONS

BACKGROUND OF THE INVENTION

1. Field of the Invention

The present invention relates to a liquid discharge device having diagnostic functions of diagnosing the discharge functions of a driving circuit for driving a discharge actuator of a liquid discharge head for discharging a liquid, and to a self-diagnosis method of the liquid discharge device. The present invention particularly relates to the art of a function for confirming that the driving circuit is in a normal state capable of discharging, before actually discharging a liquid such as medical substances, ink, or the like.

2. Description of the Related Art

Conventionally, with inhalers wherein a person inhales a substance sprayed into the throat or mouth, there have been cases wherein the following operation is necessary as a preparation of inhaling the substance, for example. That is to say, a replaceable cartridge integrally configured of a liquid tank and liquid discharging portion, detachably mounted to the inhaler main unit, is mounted to the main unit following which confirmation is made regarding whether or not the mounting has been properly made such that the liquid can be correctly discharged. There has also been cases wherein confirmation is necessary to confirm that the discharge driving circuit for discharging at the main unit side functions properly. One conceivable method for preparation before discharging and inhaling the liquid is to cause a smaller amount of liquid, such as around $1/10$ the actual amount to be inhaled, to be discharged, and to visually confirm the state of the mist discharged therefrom.

Such confirmation is also performed with printing apparatuses and the like for discharging ink, and a printing apparatus has been proposed having a function for detecting whether a printing head has been mounted or not mounted, by checking the contact state of electrical terminals.

However, such a method for visually confirming the mist state of the substance wastes the substance. Also, the method for detecting whether or not the discharge head is mounted by the state of contact at the electrical terminals only detects whether or not the discharge head is mounted, and cannot perform an overall check regarding, for example, the actuators themselves within the discharge head, such as heaters or piezoelectric elements, or the state of the driving circuit.

SUMMARY OF THE INVENTION

The present invention provides a liquid discharge device capable of checking the overall state of a discharge head driving circuit, while suppressing the amount of consumption of the liquid.

A liquid discharging device having discharging function self-diagnosis functions has a mounting portion for mounting a discharge head, wherein a driving circuit for driving the discharge head is closed by assembling the head into the device, and further has a diagnostic circuit for diagnosing the state of the driving circuit. That is to say, with the liquid discharging device, the diagnostic circuit is formed sharing part of the driving circuit, so as to directly diagnose the state of the driving circuit using the diagnostic circuit. Typically, the liquid discharging device comprises a discharge head mounting unit, a power source, a switch, and a control unit configured to control the switch. The mounting unit has first and second electrical terminals for connection to the discharge head. The power source is capable of selectively applying multiple voltages to the first electrical terminal. The switch alters the connection relation between the power source and the first and second electric terminals. Attaching the discharge head to the mounting unit closes the driving circuit for driving the discharge head. The control unit selectively realizes a state for supply of discharge power and a state for diagnosis. The control unit supplies electric power to a discharging actuator, sufficient to cause the discharging actuator to discharge liquid, by controlling the switch, in the discharge power supply state. On the other hand, in the diagnostic state, the control unit supplies electric power insufficient to cause the discharging actuator to discharge liquid to the discharging head, by controlling the switch. The voltage of at least one of the first and second terminals for connection to the discharge head is measured, and information of the state of the power source and the discharging actuator and the driving circuit is obtained.

In a further aspect, a discharge function self-diagnosis method of a liquid discharging device supplies electric power insufficient to cause the discharging actuator to discharge liquid to the discharging actuator by controlling the switch, in which state the voltage of at least one of the electrical terminals is measured, and information of the state of the power source and the discharging actuator and the driving circuit of the discharge head is obtained.

Thus, according to an embodiment of the invention, with a liquid discharging device such as a medical inhaler, printing device, or the like, information regarding the state of the driving circuit, including the discharging actuator of the discharge head that is mounted, can be obtained without wasting the liquid such as the substance or ink or the like to be discharged, and without prior observation. The diagnostic circuit is formed sharing part of the driving circuit, and the state of the driving circuit is directly diagnosed using the diagnostic circuit, so diagnosis of discharge functions can be performed more accurately. Typically, the connection relation between the power source and the first and second electrical terminals is changed by controlling the switch in a state wherein electric power insufficient to cause liquid discharging with the discharging actuator is supplied to the discharging actuator, and the voltage at the first or second electrical terminal is measured. Based on the voltage measurement value thus obtained, self-diagnosis can be performed regarding whether the driving circuit, including the discharge head, is in a normal state capable of discharging. Accordingly, the amount of discharging energy generated at the discharging actuator at the time of self-diagnosis is small, and liquid does not need to be discharged. This means that there is ordinarily no discharging of the liquid, thereby conserving what otherwise would be unnecessarily discharged and wasted, and possibly hazardous.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

The following description will be made with reference to an example of a liquid discharge device used as a medical inhaler.

Figure 1:
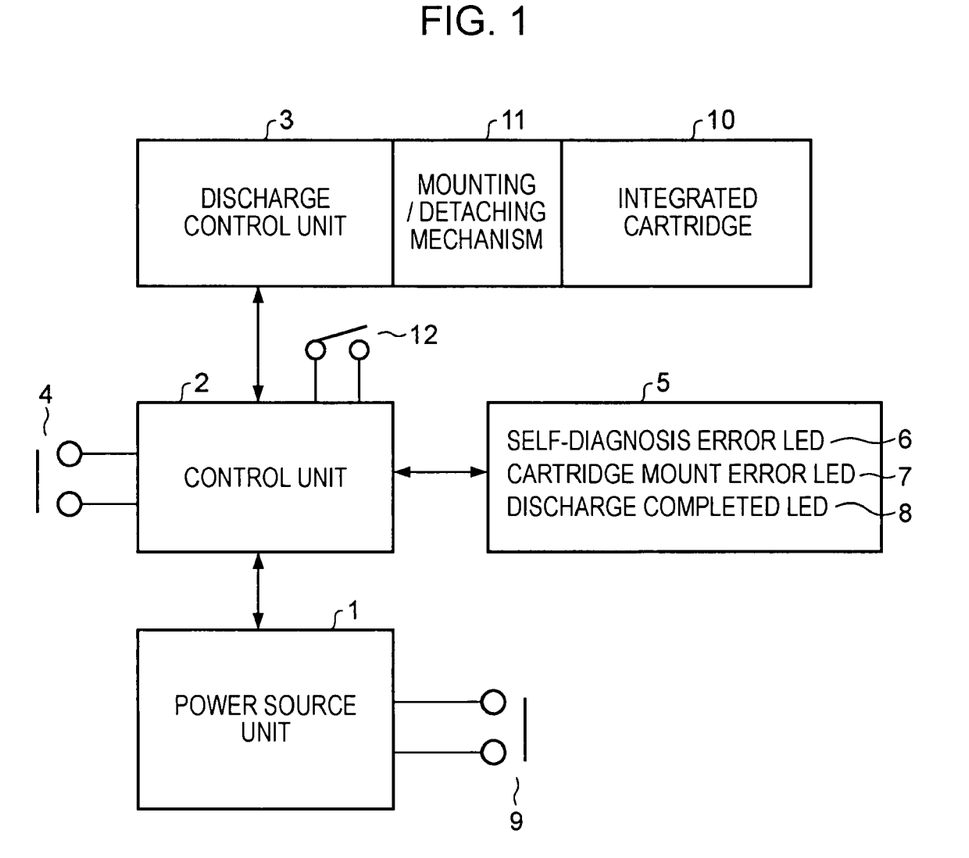
FIG. 1 is an internal configuration diagram of an inhaler according to an embodiment of the present invention.
Figure 2A:
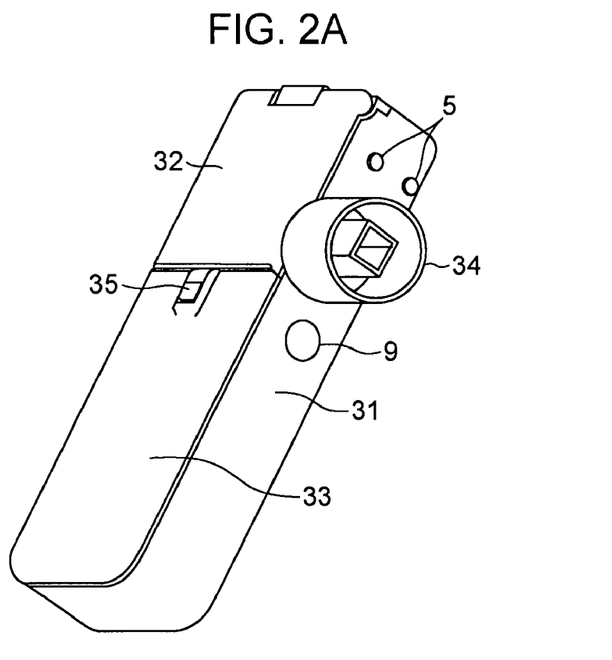
FIGS. 2A and 2B are external views of the inhaler according to the embodiment.
Figure 2B:
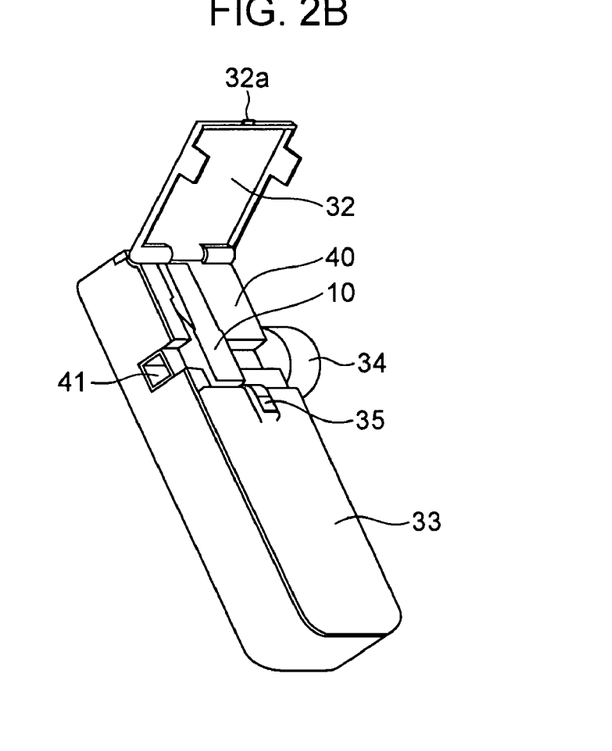
Figure 3:
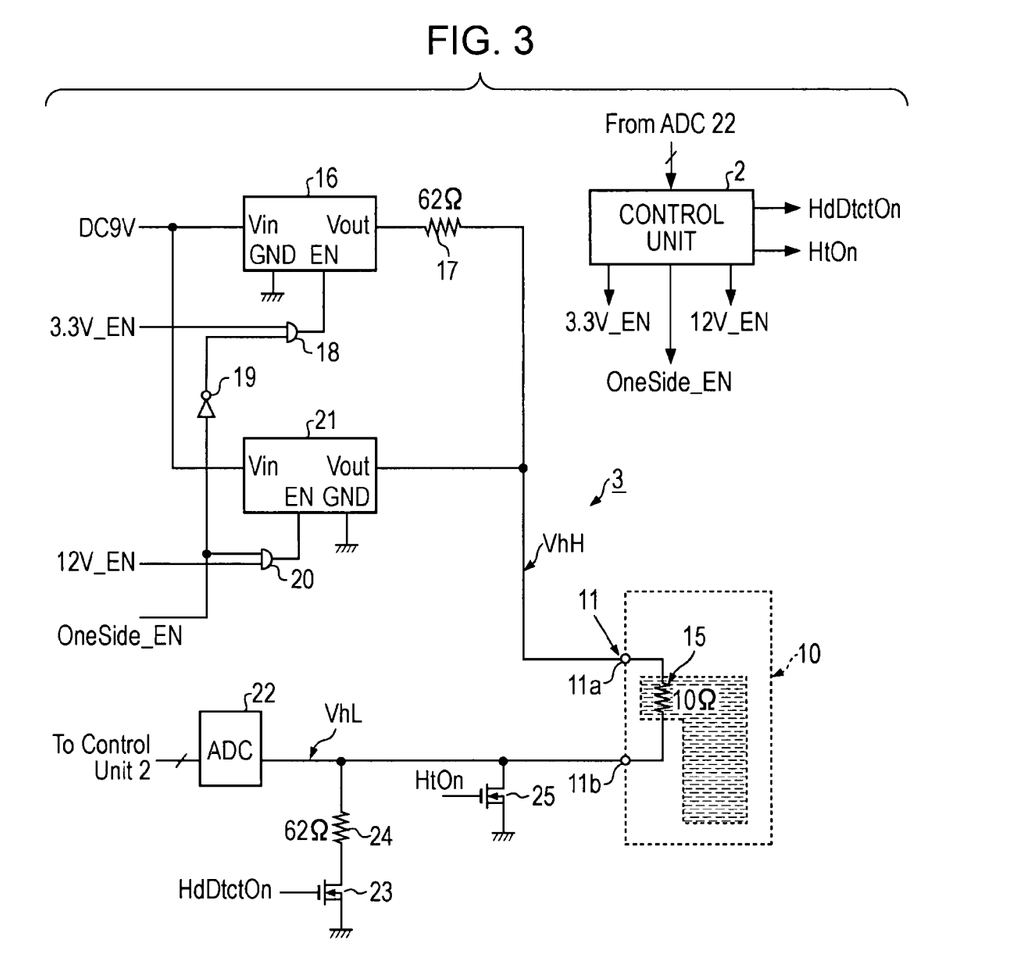
FIG. 3 is a circuit configuration diagram of a discharge control unit in the embodiment.

FIG. 1 is a block diagram illustrating the internal configuration of a medical inhaler according to the first embodiment of the present invention, FIG. 2A is a perspective view showing an inhaler, FIG. 2B shows the inhaler with an access cover 32 opened, and FIG. 3 is a diagram showing the circuit configuration of a discharge driving circuit of the inhaler.

As shown in FIG. 1, the inhaler according to the present embodiment has a control unit 2 for controlling the overall operations of the device. Electrically connected to the control unit 2 are a power source 1, discharge control unit 3, discharge activation switch (tactile switch) 4, display unit 5, cartridge cover switch 12, and so forth. The power source 1 is controlled so as to turn on and off by a power source switch (tactile switch) 9. The display unit 5 has multiple LEDs serving as a warning device for providing notification of various types of errors and other information, and includes an LED 6 for displaying self-diagnosis errors, an LED 7 for displaying cartridge mounting errors, and an LED 8 for indicating that discharging has been completed. The discharge control unit 3 performs control of discharging of a substance from the cartridge 10 detachably mounted by way of a mounting/detaching mechanism 11 serving as a discharge head mounting unit.

In FIGS. 2A and 2B illustrating an example of the inhaler housing the above-described components, a housing is configured of an inhaler main unit 31, access cover 32, and front cover 33. Reference numeral 35 denotes a lock lever. A protrusion 32a is formed on the tip of the access cover 32 which engages with the lock lever 35, so that the access cover 32 will not open when the inhaler is in use. That is to say, the protrusion 32a is formed so as to engage a claw-shaped member formed on the tip of the lock lever 35 pressed by a spring. Sliding the lock lever 35 downwards causes the access cover 32 to open on an unshown hinge by the force of an unshown access cover return spring which is pressing the access cover 32. FIGS. 2A and 2B also show the power switch 9, LEDs of the display unit 5, the cartridge 10, a mouthpiece 34 having an air intake 41, and a cartridge guide 40.

As shown in FIG. 2B which illustrates the access cover 32 in the opened position, opening the access cover 32 reveals the cartridge 10 mounted within the housing following the cartridge guide 40, and the mouthpiece 34. The mouthpiece 34 is situated below the cartridge 10, and both the mouthpiece 34 and the cartridge 10 are mounted crossing one another. The cartridge 10 has a tank for storing the liquid, a discharge head for discharging the liquid, an electrode portion (electrical connection portion) for supplying electric power, from the battery, to generate discharging energy at the discharging actuator of the discharge head. Note that while the present embodiment describes the discharging actuator as being an electrothermal converter, the present invention is not restricted to such.

FIG. 3 shows a discharge driving circuit including the discharge control unit 3 and cartridge 10. Reference numerals 11a and 11b are a pair of electrical terminals of the mounting/detaching mechanism (discharge head mounting unit) 11, each corresponding to multiple electrodes of the electrothermal converter (discharge heater 15) of the cartridge 10. (The term "contact portion" may be used herein instead of "terminal"). A DC/DC converter 21 is a primary power source, and a DC/DC converter 16 (to which a resistor 17 is serially connected) is a secondary power source, which together make up a power source capable of selectively applying multiple voltages to the first terminal 11a. A first switch unit is a power select switch for selecting one of the multiple power sources and turning on/off connection of the selected power source to the first terminal 11a. The power select switch includes two AND gates 18 and 20, and an inverter 19, connected as shown in FIG. 3. A second switch unit is a ground connect switch for switching the connection of the second terminal 11b to ground GND, and is configured of an FET 25. Switch means includes the power select switch (first switch unit) and the ground connect switch (second switch unit).

With the present embodiment, the power source is configured with a primary power source 21 capable of outputting 12 V, and a secondary power source 16 capable of outputting 3.3 V, in order to apply voltage of multiple voltage values to the first terminal 11a. However, the present invention is not restricted to this configuration, and may be an arrangement wherein optional voltage can be output from a single power source. In this case, the resistor 17 shown in FIG. 3 is not connected to a common output of the power source, but rather is connected to the output of the secondary power source 16 only. This is because sufficient heat cannot be obtained at the discharging heater 15 at the time of applying high voltage from the power source to perform discharging, were the resistor is introduced therebetween.

The resistor 17 is not indispensable to the present embodiment. However, providing the resistor 17 to the present embodiment is preferable, since the heating at the discharging heater 15 can be suppressed thereby at the time of performing discharge function diagnosis using the secondary power source. At this time, the resistance value of the resistor 17 is preferably higher than the resistance value of the discharging heater 15 and is set to 62 Ω in this embodiment.

The AD converter 22 for converting the voltage of the second terminal 11b into digital data makes up a part of a voltage measuring configuration for measuring the voltage of at least one of the first and second terminals 11a and 11b (here, for measuring the voltage of the second terminal 11b in the example shown in FIG. 3). With the present invention, the primary or secondary power source is connected to the first terminal 11a, but unless the second terminal 11b is connected to ground GND, a state is created wherein there is insufficient power to discharge liquid from the discharge head 10, in which state the voltage is measured at the AD converter 22. Based on this voltage measurement value, information of the power source and discharging actuator and discharging driving circuit state are obtained as described below.

As described with the above configuration, the power source includes a primary power source 21 capable of applying a first voltage (12 V in this first embodiment) sufficient to discharge liquid, and a secondary power source 16 capable of applying second voltage (3.3 V in this first embodiment) insufficient to discharge liquid. The power select switch, using components 18, 19, and 20, exclusively selects one of the power sources so as to be connected to the first terminal 11a.

The operational control of the overall device including switch control such as described above is executed by control effected by the control unit 2 shown in FIG. 1. Upon the control unit 2 connecting the primary power source 21 to the first terminal 11a with the power select switch, and connecting the second terminal 11b to ground GND with the FET 25 of the ground connect switch, liquid discharging is performed. The reason is that 12 V voltage drop occurs at the discharge heater 15.

With the present embodiment, the switch further includes a third switch unit which is a bleeder switch composed of FET 23 for switching the connection of the second terminal 11b via a resistor 24 to ground GND, thereby to permit a bleeder current to flow. Note however, that this bleeder switch can be omitted. Unless the ground connect unit is controlled to be on, then in the event that the primary power source 21 is connected to the first terminal 11a with the power select switch and the second terminal 11b is connected to ground GND with the bleeder switch 23, power sufficient for discharging cannot be supplied to the discharging actuator due to the presence of the resistor 24. Of course, even in the event that the secondary power source 16 is connected to the first terminal 11a with the power select switch and the second terminal 11b is connected to ground GND with the bleeder switch 23, power sufficient for discharging cannot be supplied to the discharging actuator, since even if resistor 24 were not present, power supplied by the secondary power source 16 is insufficient to cause discharge. While the resistance value of the resistor 24 is not restricted in particular, this is preferably greater than the resistance value of the discharging heater. Thus, the voltage drop at the discharge head can be kept lower at the time of discharge function diagnosis. In FIG. 3, the resistor 24 is 62 Ω.

Control of the overall operations of the device such as described above can be performed by software, carried out by a function execution arrangement, according to a program installed in the control unit 2.

The operations of the inhaler according to the present embodiment will be described with reference to FIGS. 4 through 7.

Figure 4:
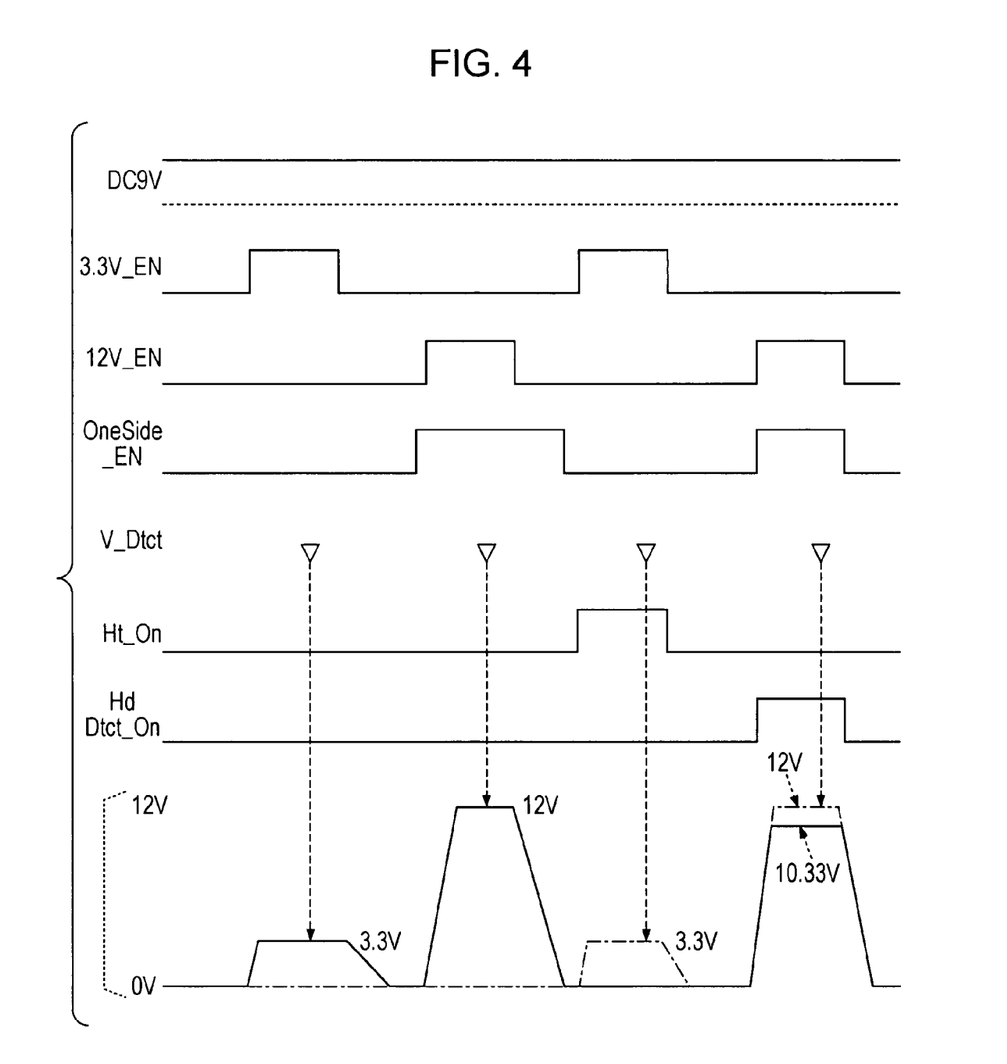
FIG. 4 is a timing chart showing processing for self-diagnosis of the discharge control unit in the embodiment.
Figure 5:
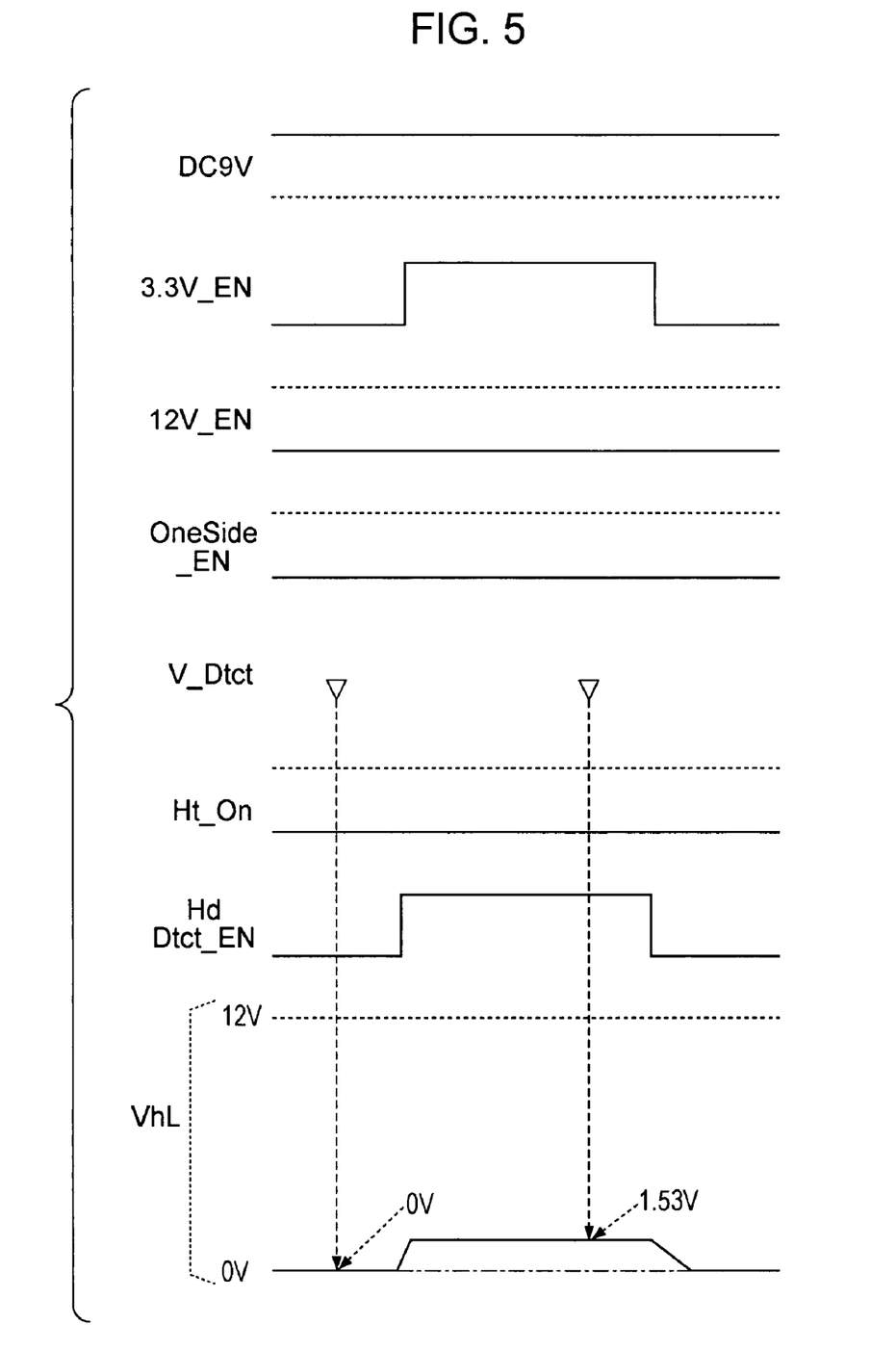
FIG. 5 is a timing chart showing cartridge mounting detection operations in the embodiment.
Figure 6:
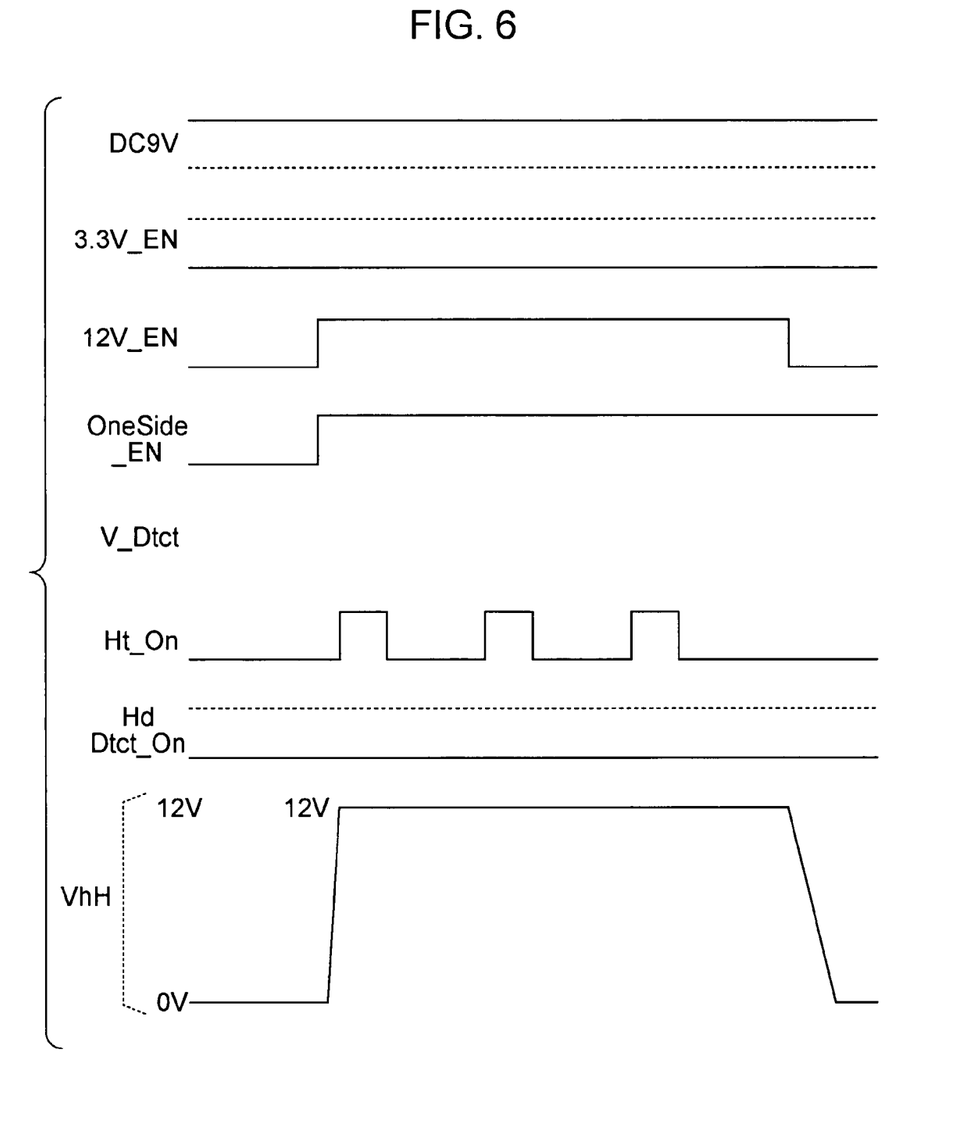
FIG. 6 is a timing chart showing discharge operations in the embodiment.
Figure 7:
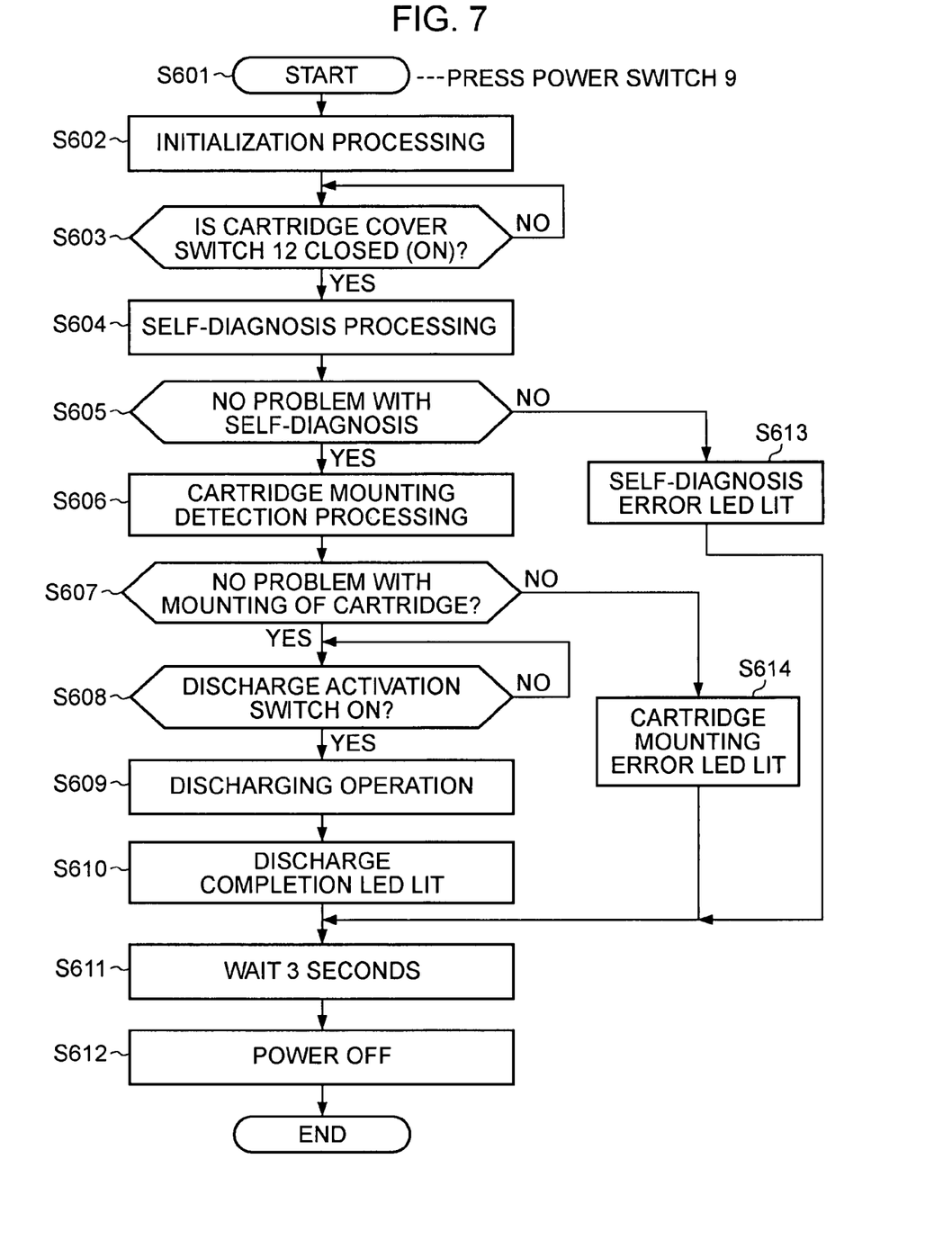
FIG. 7 is a flowchart for describing the operations of the control unit of the inhaler according to the embodiment.

FIG. 4 is a timing chart showing processing for self-diagnosis of the discharge control unit 3 of the inhaler according to the present embodiment, FIG. 5 is a timing chart showing cartridge mounting detection operations used with the inhaler according to the present embodiment, FIG. 6 is a timing chart showing discharge operations at the time of discharging the substance with the inhaler according to the present embodiment, and FIG. 7 is a flowchart for describing the operations of the control unit 2 of the inhaler according to the present embodiment.

Description will now proceed following the flowchart in FIG. 7. First, in step S601 ("step S" will hereafter be written simply as "S") upon the user pressing the power switch 9, the power source 1 of the inhaler turns on. Subsequently, in the initialization processing in S602, the control unit 2 turns off the self diagnosis error LED 6, cartridge mounting error LED 7, and discharge completion LED 8. Also, the control unit 2 initializes the discharge control unit 3 shown in FIG. 3 to the signal state at the left side in the timing chart in FIG. 4.

Next, in S603, the control unit 2 determines whether or not a cartridge cover switch 12 (e.g., a switch for detecting the state of the access cover 32 shown in FIG. 2) is closed (ON). In the results of determination are NO, the flow returns to S603, and if YES the flow proceeds to S604.

In the self-diagnosis processing in S604, the control unit 3 sets the 3.3 V_EN for the discharge control unit (see FIG. 3) to high. Accordingly, this means that the 3.3 V output from the secondary power source 16 is applied to the first terminal 11a by action of the power select switch. Following a predetermined amount of time (V_Dtct timing ∇) elapsing from output of this High level, the control unit 2 converts the VhL voltage (voltage at the second terminal 11b side) into digital data at AD converter 22 and reads it. This checks whether or not the cartridge 10 has been mounted at the first and second terminals 11a and 11b of the mounting/detaching mechanism 11, and whether or not the secondary power source 16 has achieved 3.3 V output. A voltage of 3.3 V is expected in a correct operational condition, since both of the ground connect switch and the bleeder switch are open. In the event that 3.3 V is measured from the AD converter 22, confirmation is made that the cartridge 10 is mounted properly, and that the secondary power source 16 is outputting 3.3 V.

Subsequently, the 3.3 V_EN is set to Low output, and the 12 V_EN and OneSide_EN are set to High output. This applies the 12 V output from the primary power source 21 to the first terminal 11a, by action of the power select switch. Following a predetermined amount of time (V_Dtct timing ∇) after the two signals being set to High output, the control unit 2 converts the VhL voltage into digital data at the AD converter 22 and reads it. Here, there is a check of whether or not the cartridge 10 is mounted at the first and second terminals 11a and 11b, and whether or not the primary power source 21 has achieved 12 V output (which is the discharging voltage enabling discharging at the cartridge 10). A voltage of 12 V is expected in a correct operation condition, since both of the ground connect and bleeder switches are still open. If normal so far, this also serves as confirmation that the power select switch configured of the AND gates 18, 20, and so forth, is operating properly, as well.

Subsequently, the 12 V_EN and OneSide_EN are set to Low output, and the 3.3 V_EN and the Ht_On to the gate of the FET 25 are set to High output, so as to close the ground connect switch and the supply power form the secondary power source 16. Following a predetermined amount of time (V_Dtct timing ∇), the control unit 2 converts the VhL voltage into digital data at the AD converter 22 and reads it. Here, whether or not the FET 25 of the second switch is operating normally is checked. A voltage of 0 V is expected in a correct operational condition, since the ground connect switch is closed. If 0 V is measured from the AD converter 22, this confirms that a closed circuit including the secondary power source 16 and the discharging heater 15 of the cartridge 10 is established. Here, the confirmation in the 3.3 V output diagnosis processing to the farthest left in FIG. 4 is a prerequisite. An arrangement may be made wherein the processing so far is performed, and the self-diagnosis processing in S604 is ended and the flow proceeds to the discharging operations.

The diagnosis so far confirms that the discharge head is correctly mounted, that the output voltages of the primary power source 21 and the secondary power source 16 are normal, that the components of the power select switch are operating correctly, and that the FET 25 of the ground connect switch is normal. Accordingly, normal discharge can be performed.

However, the following process is preferably continued to carry out diagnosis in a more sure manner.

Subsequently, the 3.3 V_EN and Ht_On are set to Low output, and the 12 V_EN, OneSide_EN, and the HdDtct_ON to the gate of the FET 23 of the bleeder switch are set to High output, so as to supply power form the primary power source 21 and to close the bleeder switch. Following a predetermined amount of time (V_Dtct timing ∇), the control unit 2 converts the VhL voltage into digital data at the AD converter 22 and reads it. Here, whether or not the FET 23 of the bleeder switch is operating normally, and further, the resistance value of the discharging heater 15, are checked. A predetermined voltage drop from 12 V (in the present embodiment, 12−10.33≈10/(10+62)×12) is expected in a correct operational condition, since only a bleeder current is flowing. If the predetermined voltage drop is measured from the AD converter 22, this confirms that the heater 15 has the predetermined resistance value (10 Ω in the present embodiment). Here, the confirmation in the 12 V output diagnosis processing the second from the left in FIG. 4 is a prerequisite.

Subsequently, the 12 V_EN, OneSide_EN, and the HdDtct_ON are set to Low output. Thus, the flow proceeds to S605 (ending of self-diagnosis operations), where determination is made regarding whether or not there is no problem with the self diagnosis results. In the event that the read values (VhL) at the four timings ∇ of V_Dtct are the values indicated by solid lines (∇) determination is made that all are without problem. Now, in the event that the result of determination in S605 is NO (e.g., in the event that the read value (VhL) is as indicated by the dotted line), the flow proceeds to S613, but if YES, the flow proceeds to S606. In S613, since there has been a determination that a self-diagnosis error has occurred, the self-diagnosis error LED 6 is lit, and the flow proceeds to S611 where the unit is powered off after a short delay.

On the other hand, in S606, cartridge mounting detection processing is performed. This processing in S606 follows the processing shown in the cartridge mounting detection operation timing chart shown in FIG. 5. First, the 3.3 V_EN and HdDtct_ON are set to High output so as to select the secondary power source 16. Now, the secondary power source 16 and the FET 23 of the bleeder switch have already been confirmed to be normal. Following a predetermined amount of time (V_Dtct timing ∇), the control unit 2 converts the VhL voltage into digital data at the AD converter 22 and reads it. A voltage of approximately 1.53 V is expected (3.3 V×62/(62+62+10)) since only a bleeder current is flowing. If approximately 1.53 V is detected, this means that the discharge head is mounted correctly. That is to say, due to the calculation 3.3×62/134≈1.53, mounting of the cartridge 10 and the resistance value of the heater 15 is checked in a more sure manner. This process can be omitted.

Subsequently, 3.3 V_EN and HdDtct_ON are set to Low output, and the flow proceeds to S607. In S607, whether or not mounting of the cartridge is without problem is determined. In the event that approximately 1.53 V is not detected this yields NO, so the flow proceeds to S614 where the carriage mounting error LED 7 is lit, and the flow proceeds to S611, where, as before, the unit is powered off after a short delay. On the other hand, in the event that approximately 1.53 V is detected, this yields YES, so the flow proceeds to S608. In S608, whether or not the discharge activation switch 4 has been pressed is determined. If NO, the flow remains in S608, and if YES, the flow proceeds to S609.

In S609, discharging operations are executed following the timing chart shown in FIG. 6. First, the 12 V_EN and OneSide_EN are set to high output so as to select primary power supply 21. Subsequently, the Ht_On is set to high-pulse output for a predetermined time, so as to pulse the ground connect switch closed for the predetermined time. Thereafter, following a predetermined interval, Ht_On is set to high-pulse output for a predetermined time again. Repeating the high-pulse output from a predetermined number of times discharges the substance form the cartridge 10, the amount thereof having been predetermined and stored in the control unit 2.

Subsequently, 12 V_EN and OneSide are set to Low output, and the flow proceeds to S610. In S610, determination is made that discharging has ended upon having discharged the predetermined amount of the substance, the discharge completed LED 8 is lit, and the flow proceeds to S611. In S611, one of the LEDs 6, 7, and 8 is lit for 3 seconds, and then the flow proceeds to S612. In S612, the power source supply of the power source unit 1 is turned off, and operations end (END).

Note that in the above self-diagnosis, the form of the self-diagnosis processing timing chart shown in FIG. 4 changes according to what degree of discharging function self-diagnosis is performed. That is to say, changing the manner of control of the switch with the control unit enables various combinations of components in the closed circuit including the power source and discharging heater 15 of the cartridge 10. This can be determined as requested. However, from the perspective of the present invention at least a check for mounting of the discharge head, a voltage check for the discharge voltage supply, and a check for the switch for executing discharging, are typically necessary.

For example, in the event that there is no need to check the resistance value of the heater 15 of the cartridge 10, the three diagnosis checks to the left in FIG. 4 are sufficient. The reason is that these diagnosis processes carry out checking of the primary power source 21 for discharge voltage supply in the closed circuit including the power source and discharging heater 15 of the cartridge 10, and checking of the FET 25 of the ground connect switch for executing discharging, are performed. The former is performed in the second diagnosis processing from the left in FIG. 4, and the latter is performed in the first and third diagnosis processing from the left in FIG. 4. Further, a check of mounting of the cartridge 10 to the mounting/detaching mechanism 11 is also performed to some extent in these diagnosis processes, so the carriage mounting detection operations shown in FIG. 5 can be omitted. Also, an arrangement may be made wherein the diagnosis process to the far right in FIG. 4 is not performed and the carriage mounting detection operations shown in FIG. 5 are performed instead, so as to check the mounting of the cartridge 10 and the resistance value of the heater 15 in a more sure manner. The diagnosis processing shown in FIG. 5 can execute checking of mounting of the cartridge and resistance value of the heater 15 in a state wherein the possibility of liquid being discharged is smaller than with the diagnosis processing to the far right in FIG. 4.

It should be noted that the voltage values, resistance values, and other numbers in the above embodiment are only exemplarily illustrated figures, and actual values may be other values.

While the voltage of the second electric terminal 11b has been described as being read by the AD converter 22 in the above-described embodiment, the voltage of the first electric terminal 11a may be read with the present embodiment. The following is a description of the self-diagnosis procedures for such a case.

As a first step, the control unit 2 performs settings such that

OneSide_EN=Low, 3.3 V_EN=High, and

HtOn=Low.

Due to this processing, the 3.3 V output is controlled to on, the 12 V output to off, and the FET 25 to off. Accordingly, the 3.3 V output from the secondary power source 16 is applied to the first terminal 11a. Following a predetermined amount of time following the output, the control unit 2 converts the voltage at the first terminal 11a side into digital data at the AD converter 22 and reads it. Here, whether or not the secondary power source 16 has achieved 3.3 V output is checked. In the event that 3.3 V is measured from the AD converter 22, confirmation is made that the secondary power source 16 is outputting 3.3 V correctly.

As a second step, the control unit 2 performs settings such that

OneSide_EN=High,

12 V_EN=High, and

HtOn=Low.

Due to this processing, the 3.3 V output is controlled to off, the 12 V output to on, and the FET 25 to off. Accordingly, the 12 V output from the primary power source 21 is applied to the first terminal 11a. Following a predetermined amount of time following the output, the control unit 2 converts the voltage at the first terminal 11a side into digital data at the AD converter 22 and reads it. Here, whether or not the primary power source 21 has achieved 12 V output is checked. In the event that 12 V is measured from the AD converter 22, confirmation is made that the primary power source 21 is outputting 12 V correctly.

These two steps enable whether or not the power select switch is normal, to be determined.

As a third step, the control unit 2 performs settings such that

OneSide_EN=Low, 3.3 V_EN=High, and

HtOn=High.

Due to this processing, the 3.3 V output is controlled to on, the 12 V output to off, and the FET 25 to on. Accordingly, the 3.3 V output from the secondary power source 16 is applied to the first terminal 11a, the discharging heater, the second terminal 11b, FET 25, and on to the ground GND. Following a predetermined amount of time after effecting this control, the control unit 2 converts the voltage at the first terminal 11a side into digital data at the AD converter 22 and reads it. Now, whether or not the read value within the range of 0.41 V to 0.51 V is detected. If within this range, it can be said that the 3.3 V output voltage is voltage that has been divided by the 62Ω resistor 17 and the 10 Ω discharging heater 15, so it can be determined that the 3.3 V output (i.e., the secondary power source 16), the 62 Ω resistor 17, the discharging heater 15, the FET 25, and the ground GND are correctly connected and properly functioning.

That is to say, in the event of reading the voltage of the first electrical terminal 11a, diagnosis can be even made regarding whether or not the discharging heater 15 has the predetermined resistance value, without providing the FET 23 and resistor 24, which form the bleeder switch.

Figure 8:
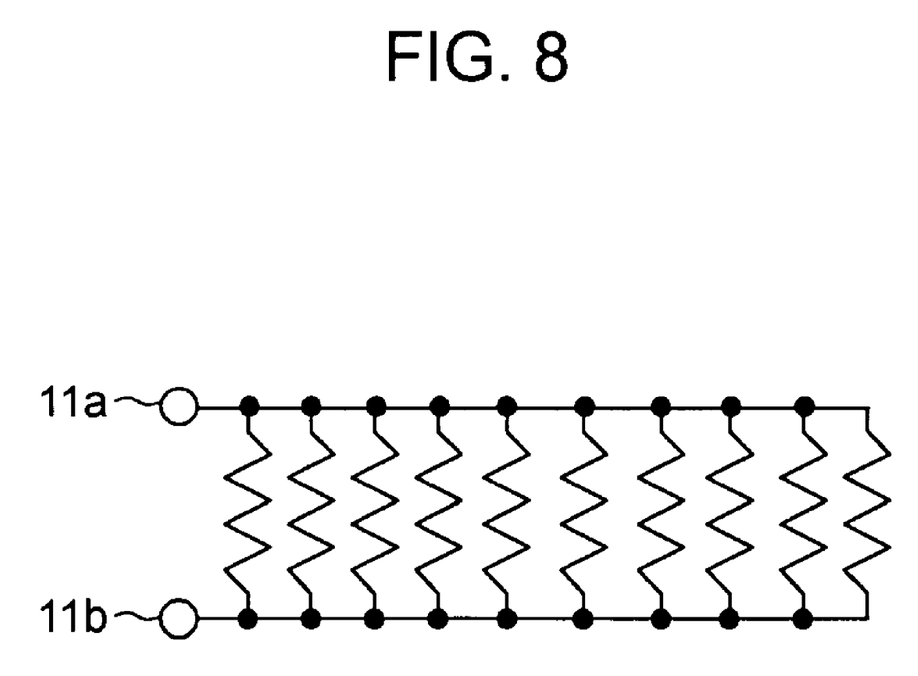
FIG. 8 is a circuit diagram of a discharging actuator used in one embodiment of the invention.

Note that while the discharging heater 15 of the cartridge 10 has been shown in a simplified manner as a single resistance, an actual discharge head has an array of multiple nozzles in FIG. 3. That is to say, multiple discharge heaters are connected in array. For example, the value 10 Ω of the discharge heater 15 as shown in FIG. 8 may be 10 Ω as a result of ten 100 Ω heaters being arrayed in parallel, so as to configure a discharging actuator having ten nozzles.

Figure 9:
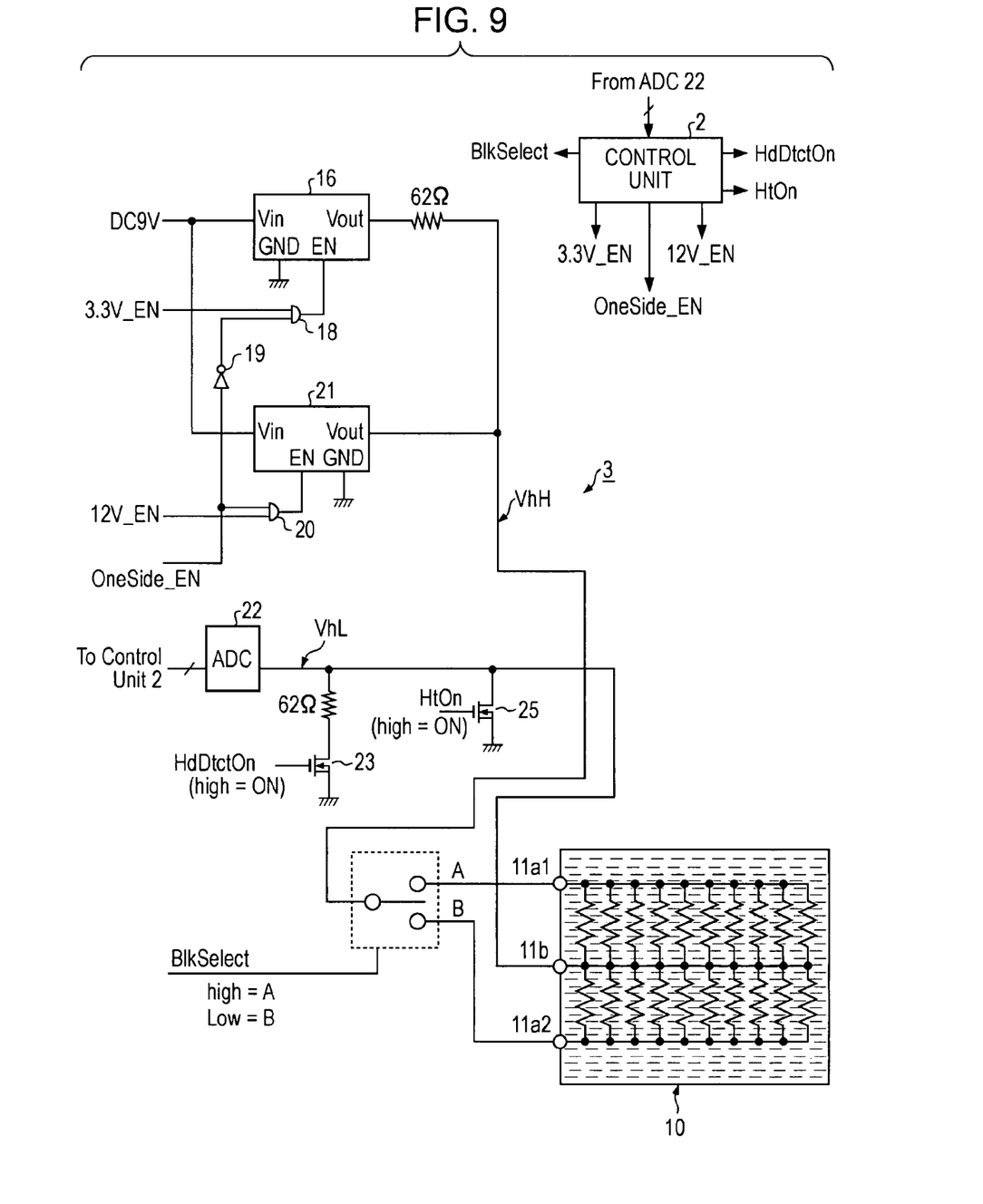
FIG. 9 is a circuit configuration diagram of the discharge control unit according to another embodiment of the present invention.

The relation in connection of multiple heaters, in an arrangement wherein a discharge head having multiple discharging heaters is mounted to the discharge head mounting unit, is shown in exemplary form in FIG. 9. FIG. 9 is a block configuration wherein there are two rows of the above nozzle arrays with ten nozzles in array. The second electric connector portion 11b serves as the shared heater terminal for the two blocks of discharge nozzle groups (ten each). Also, two first electric terminal 11a are provided as 11a1 and 11a2, so as to be able to drive heating of the discharge heaters in time-division for each of the blocks separately. Moreover, the control unit 2 is configured so as to be able to selectively connect the VhH signal to the terminals 11a1 and 11a2, whereby nozzles in multiple block configurations can be handled as well.

The present invention can be widely applied for realization of a discharging function self-diagnosis function and method in liquid discharging devices (medical inhalers, printing devices, etc.) using a detachable discharge head which discharges a liquid with a discharging actuator such as a resistor or piezoelectric element or the like. Accordingly, while the present invention has been described by way of an example of a medical inhaler in the above embodiments, the present invention is not restricted to this. Still, the present invention is more preferably used as a medical inhaler. In this case, a liquid including a medical substance, such as liquid medication or a liquid in which a medical solution has been dispersed or the like, is preferably discharged. Also, the liquid being discharged may be discharged as droplets, or droplets thereof may be formed following discharging.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-107082 filed Apr. 10, 2006, which is hereby incorporated by reference herein in its entirety.

What is claimed is:

1. A medical inhaler device comprising:
    a discharge head mounting unit configured with first and second electrical terminals;
    a power source;
    a switch configured to alter electrical connection between said power source and said mounting unit; and
    a control unit configured to control said switch;
    wherein a driving circuit for driving a discharge head is closed by attaching said discharge head to said mounting unit, and wherein said discharge head includes a discharging actuator, configured to discharge liquid;
    wherein said power source is configured so as to be able to selectively output a plurality of voltages; and
    wherein said control unit selectively effects
        a discharge electrical power supply state, wherein electric power sufficient to cause the discharging actuator to discharge liquid is supplied to said discharge head, by controlling said switch, and
        a diagnostic state, wherein electric power insufficient to cause said discharging actuator to discharge liquid is supplied to said discharging head by controlling said switch, the voltage of at least one of the first and second terminals is measured, and information of the state of said power source and said discharging actuator and said driving circuit is obtained.

2. The medical inhaler device according to claim 1, said power source further including a primary power source for outputting a first voltage to said discharging actuator, of electric power sufficient to cause said discharging actuator head to discharge liquid, and a secondary power source for outputting a second voltage to said discharging actuator, of electric power insufficient to cause said discharging actuator head to discharge liquid;

wherein said switch is configured to select one or the other of said primary power source and said secondary power source, and further includes a power select switch for selecting one or neither or said primary and secondary power sources for connection to said first electrical terminal as one output of the selected power source, and a ground select switch connecting said second electrical terminal to ground; and wherein said control unit has a discharging function for causing said discharge head to discharge liquid by controlling said switch so as to turn on connection of said primary power source to said first electrical terminal, as well as to turn on connection of said second electrical terminal to ground, thereby realizing a discharge power supply state, and a diagnostic function wherein said switch is controlled so as to turn on connection of either said primary or said secondary power source to said first electrical terminal as one output of the power source, creating a state in which electric power insufficient to cause said discharging actuator to discharge liquid is supplied to said discharging actuator, in which state the voltage of at least one of the first and second electrical terminals is measured, and information of the state of said power source and said discharging actuator and said driving circuit is obtained.

3. The medical inhaler device according to claim 2, said switch further including a bleeder switch, configured to turn on and off contact to said second electrical terminal via resistance;

wherein in said diagnostic function, said switch is controlled so as to turn on connection of either said primary or said secondary power source to said first electrical terminal, and also so as to turn on connection of said second electrical terminal by said bleeder switch, creating a state in which electric power insufficient to cause said discharging actuator to discharge liquid is supplied to said discharging actuator, in which state the voltage of at least one of the first and second electrical terminals is measured, and information of the state of said power source and said discharging actuator and said driving circuit is obtained.

4. The medical inhaler device according to claim 3, wherein the resistance value of said resistance, via which said bleeder switch connects said second electrical terminal to ground, is greater than the resistance value which said discharge head exhibits.

5. The medical inhaler device according to claim 1, wherein the discharging actuator of said discharge head is an electro-thermal converter or a piezoelectric element.

6. A discharge function self-diagnosis method of a medical inhaler device including a discharge head mounting unit configured with first and second electrical terminals, wherein said mounting unit is configured for electrical connection via said first and second terminals to a driving circuit of a discharge head which includes a discharging actuator for discharging the liquid, a power source, a switch configured to alter electrical connection between said power source and said mounting unit, and a control unit configured to control said switch;

wherein electric power insufficient to cause said discharging actuator to discharge liquid is supplied to said discharging actuator by controlling said switch, the voltage of at least one of the first and second electrical terminals is measured, and information of the state of said power source and said discharging actuator and said driving circuit of the discharge head is obtained.

7. The discharge function self-diagnosis method of a medical inhaler device according to claim 6, wherein the electrical connection between said power source and mounting unit is altered by controlling said switch, thereby obtaining information of the contact state between said discharge head and said first and second electrical terminals in the driving circuit of said discharge head, the value of voltage applied to said first electrical terminal as the one output of said power source, and the function of said switch for connecting to said second electrical terminal as the other output of said power source.

8. The discharge function self-diagnosis method of a medical inhaler device according to claim 7, wherein the electrical connection between said power source and said mounting unit is altered by controlling said switch, thereby obtaining information of the resistance value which said discharging actuator exhibits in the driving circuit of said discharge head.

* * * * *